(12) United States Patent
Klapproth et al.

(10) Patent No.: US 7,312,867 B2
(45) Date of Patent: Dec. 25, 2007

(54) METHOD AND DEVICE FOR THE DETECTION OF AT LEAST ONE LUMINESCENT SUBSTANCE

(75) Inventors: Holger Klapproth, Freiburg (DE); Mirko Lehmann, Freiburg (DE)

(73) Assignee: Micronas Holding GmbH (DE)

( * ) Notice: Subject to any disclaimer, the term of this patent is extended or adjusted under 35 U.S.C. 154(b) by 293 days.

(21) Appl. No.: 10/529,048

(22) PCT Filed: Sep. 12, 2003

(86) PCT No.: PCT/EP03/10144

§ 371 (c)(1),
(2), (4) Date: Mar. 24, 2005

(87) PCT Pub. No.: WO2004/031747

PCT Pub. Date: Apr. 15, 2004

(65) Prior Publication Data

US 2006/0055042 A1     Mar. 16, 2006

(30) Foreign Application Priority Data

Sep. 27, 2002  (DE)  ................. 102 45 432

(51) Int. Cl.
   *G01J 3/30*  (2006.01)
(52) U.S. Cl. .................................... 356/317
(58) Field of Classification Search ........... 356/317; 385/12

See application file for complete search history.

(56) References Cited

U.S. PATENT DOCUMENTS 4,703,182 A * 10/1987 Kroneis et al. .......... 250/458.1

4,868,103 A    9/1989  Stavrianopoulos et al.

(Continued)

FOREIGN PATENT DOCUMENTS

DE          19725050 A1    12/1998

(Continued)

OTHER PUBLICATIONS

Corst Jens, Paul et al.; Use of Up-Converting Phosphor Reporters in Lateral-Flow Assays to Detect Specific Nucleic Acid Sequences: A Rapid, Sensitive DNA Test to Identify Human Papillomavirus Type 16 Infection; (2001); pp. 1885-1893.

*Primary Examiner*—Gregory J. Toatley, Jr.
*Assistant Examiner*—Kara Geisel
(74) *Attorney, Agent, or Firm*—The Webb Law Firm

(57) ABSTRACT

Disclosed is a device for detecting at least one luminescent substance, comprising a radiation source for emitting excitation radiation to the at least one luminescent substance. The excitation radiation is provided with at least one excitation wavelength at which the luminescent substance is excited so as to emit luminescent radiation. At least one radiation receiver is provided, which detects the luminescent radiation and is configured regarding the spectral sensitivity thereof in such a way that said radiation receiver is insensitive to the radiation emitted by the radiation source. The luminescent substance is located inside a measuring chamber that is essentially impermeable to the luminescent radiation and comprises at least one wall area which is transparent to the excitation radiation emitted by the radiation source. The radiation source is placed outside the measuring chamber such that the excitation radiation emitted by the radiation source is coupled into the inside of the measuring chamber by penetrating said wall area.

12 Claims, 6 Drawing Sheets

U.S. PATENT DOCUMENTS

| | | |
|---|---|---|
| 5,061,076 A | 10/1991 | Hurley |
| 5,278,048 A * | 1/1994 | Parce et al. ............... 435/287.9 |
| 5,774,214 A | 6/1998 | Prettyjohns |
| 5,885,843 A | 3/1999 | Ayers et al. |
| 6,274,085 B1 | 8/2001 | Hollering et al. |
| 6,325,977 B1 | 12/2001 | Theil |
| 6,701,032 B1 * | 3/2004 | Freeman et al. ............... 385/12 |

FOREIGN PATENT DOCUMENTS

| | | |
|---|---|---|
| DE | 19808936 A1 | 9/1999 |
| DE | 19940751 A1 | 3/2000 |
| DE | 19844713 A1 | 4/2000 |
| DE | 10036457 A1 | 2/2002 |
| EP | 0 640 828 A1 | 3/1995 |
| EP | 0 723 146 A1 | 7/1996 |
| EP | 0 953 835 A1 | 11/1999 |

* cited by examiner

METHOD AND DEVICE FOR THE DETECTION OF AT LEAST ONE LUMINESCENT SUBSTANCE

BACKGROUND OF THE INVENTION

(1) Field of the Invention

This invention relates to a device for the detection of at least one luminescent substance, with a radiation source for the emission of excitation radiation to the at least one luminescent substance, whereby the excitation radiation has at least one excitation wavelength at which the luminescent substance is excited to emit luminescent radiation, and with at least one radiation receiver which is insensitive to the excitation radiation for the detection of the luminescent radiation, whereby the luminescent substance is located in the interior of a measurement chamber which is essentially impermeable to the radiation to which the radiation receivers are sensitive, and whereby the radiation source is located outside the measurement chamber such that the excitation radiation is injected through a wall area of the measurement that faces the radiation source and is transparent for the excitation radiation though the measurement chamber into the interior of the measurement chamber.

(2) Description of the Prior Art

A similar device of the prior art is described in EP-A-0 640 828. It has a measurement chamber which has a wall area that is formed by a dichroitic mirror, behind which, outside the measurement chamber, a radiation source is located which emits an excitation radiation through the wall area at a wavelength of approximately 302 nm (UV) into the measurement chamber. In the interior of the measurement chamber, a plurality of reaction vessels are provided, in which samples are located that are marked with a luminescent substance. The luminescent substance is excited by the excitation radiation to emit a luminescence radiation, the wavelength of which is different from that of the excitation radiation. The measurement chamber is impermeable for the luminescent radiation. For the detection of the luminescent radiation, a CCD camera is located in the measurement chamber at some distance from the samples. This device of the prior art has a relatively complicated construction.

A device of the prior art described in U.S. Pat. No. 4,868,103 has a flashlamp as the radiation source and a photomultiplier tube as the radiation receiver. Between the radiation source and a sample that contains a luminescent substance to be tested on one hand, and between the sample and the radiation receiver on the other hand, there are respective optical interference filters. This device of the prior art is therefore correspondingly expensive.

U.S. Pat. No. 5,885,843 describes another device of the prior art with a measurement chamber in which a photoluminescence aerogel is located. As the radiation source, outside the measurement chamber a UV lamp is provided which emits UV radiation into the measurement chamber through an optical filter. The UV radiation excites the photoluminescent aerogel to emit visible luminescent light which is detected with a photodiode. To prevent the light emitted by the radiation source from reaching the photodiode, the optical filter is impermeable to the luminescent light. This device of the prior art also has a relatively complicated construction.

The object of the invention is therefore to create a device of the type described above which, with a simple and compact construction.

SUMMARY OF THE INVENTION

This invention teaches that the wall area is formed by a semiconductor substrate, and that the at least one radiation receiver is integrated in the form of a semiconductor component into the semiconductor substrate.

The semiconductor substrate thereby advantageously performs a dual function, and in addition to acting as the support for the at least one radiation receiver, also acts as a window for the injection of the excitation radiation into the measurement chamber. The measurement chamber can then be manufactured particularly economically using Microsystems engineering methods. The device can thereby have very compact dimensions. The measurement chamber shields, in the wavelength range that can be detected with the radiation receiver, the at least one radiation receiver that is located in the measurement chamber or within its external contour against scattered or spurious radiation that occurs outside the measurement chamber. Any spurious radiation that penetrates into the wall of the measurement chamber is thereby either completely extinguished or is at least so severely attenuated that after it penetrates the wall it is practically no longer detected by the radiation receiver. Thus, in the wavelength range to be detected, the measurement has a high level of protection against interference from scattered or spurious radiation.

The device can optionally also be used as an optical coupler. In that case, the radiation source for the transmission of a signal can be connected with a modulation device device [sic] and the radiation receiver can be connected with a demodulation device. The term "luminescence" as used here means all emissions of radiation quanta, primarily luminous phenomena such as fluorescence or phosphorescence, that substances exhibit after quantum excitation.

In one advantageous configuration of the invention, the semiconductor substrate is a silicon substrate. Silicon is permeable for infrared light at a wavelength of greater than approximately 1080 nm, which means that the radiation source for the excitation of the luminescent substance can be provided in the form of an infrared radiation source. The radiation receiver can be a silicon photodiode that is integrated into the semiconductor substrate and is insensitive in this wavelength range.

In one particularly advantageous realization of the invention, the device is realized in the form of a thermal imaging camera which has a plurality of radiation receivers arranged in the measurement chamber, preferably in the form of a two-dimensional matrix, associated with at least one of which receivers is an optical imaging system for the imaging of the radiation source on the radiation receiver. In this case, in the interior of the measurement chamber, there can be a layer of luminescent substance that extends continuously over the radiation receiver. It is also conceivable, however, that the layer of luminescent substance has interruptions between the radiation receivers. The layer of luminescent substance can optionally occupy all of the space between the walls of the measurement chamber located one on either side of the layer of luminescent substance, i.e. the walls form a laminated stack with the layer of luminescent . . . substance. The optical imaging system is preferably located outside the measurement chamber, between the measurement chamber and the radiation source.

In one preferred embodiment of the invention, the luminescent substance is realized so that the wavelength of the luminescent radiation is less than the excitation wavelength. Upward-converting luminescent substances of this type are described in the prior art, such as EP 0 723 146 A1, for example. Examples of upward-converting luminescent substances are the BND pigment manufactured by Dyomics GmbH, Jena and IR-140. In contrast to downward-converting luminescent substances, upward-converting luminescent substances acquire the energy necessary for the quantum emission not from a single quantum effect, but from a plurality of quantum effects. Upward-converting luminescent substances therefore have, in comparison to downward-converting luminescent substances, a significantly greater Stokes shift, at which the wavelength of the excitation radiation can be, for example, twice as great as the wavelength of the luminescent radiation. Consequently it is possible to provide, as the radiation source, an infrared semiconductor radiation source, in particular a semiconductor diode, which makes it possible to have a high radiation intensity with compact dimensions. The infrared light from such semiconductor radiation sources also has the advantage that fewer spurious effects occur than with short-wave optical radiation. By means of the upward-converting luminescent substance, the optical radiation emitted by the semiconductor radiation source can be converted into visible light or into near-infrared light, so that an economical opto-electronic semiconductor sensor can be provided as the radiation receiver, which has a high detection sensitivity in this wavelength range.

It is advantageous if a boundary wall of the measurement chamber that is opposite the wall area is realized in the form of a reflector for the reflection of the excitation radiation. The radiation injected into the measurement chamber can then be used more efficiently for the excitation of the at least one luminescent substance.

In an additional advantageous realization of the invention, the wall area is connected with the interior of the measurement chamber by means of an optical waveguide, whereby the waveguide preferably runs parallel to the plane of extension of the wall area, in particular on its inside facing the luminescent substance. The radiation provided for the excitation of the luminescent substance is then conducted with particularly low losses into the interior of the measurement chamber, so that there is a uniform excitation of the luminescent substance along the semiconductor substrate. The excitation of the luminescent substance, which is preferably located on the totally reflective boundary surface of the waveguide or immediately adjacent to it, occurs by means of the evanescence field of the radiation guided in the waveguide. The radiation can be injected into the waveguide by means of a prism and/or an optical lattice on which the radiation is deflected so that it subjected to total reflection when it strikes a boundary surface of the waveguide.

In one advantageous realization of the invention, a measurement signal output of at least one radiation receiver is connected directly or indirectly by means of an analysis device with a transponder for the transmission of the measurement signal or of a signal derived from it to a receiver part, whereby the transponder is preferably integrated into the semiconductor substrate. The measurement signal measured by means of at least one radiation receiver can then be transmitted wirelessly to the receiver section and from there to an analysis section, to a display device and/or a data storage component. In that case, the device is particularly well suited for mobile use. Optionally it is also possible to connect the measurement chamber with an object or to integrate it in said object, to make it possible to verify the genuineness of the object. In that case, the object can be a credit card, a bill or banknote or an item of clothing (designer clothing), for example. To verify the genuineness of the object, the measurement chamber located on it is irradiated with the excitation light and the measurement signal measured by means of the radiation receiver is compared with a reference signal.

In one embodiment of the invention, in the interior of the measurement chamber there are at least two luminescent substances with excitation wavelengths that are different from each other, whereby associated with each of these luminescent substances is a radiation source with a spectral distribution that is adapted to the excitation wavelength of the respective luminescent substance. The radiation sources can then be optionally modulated and in particular turned on and off in alternation. By means of a comparison of the measurement signal of the radiation receiver with the modulation signal, it can be determined whether the appropriate luminescent substance is or is not present in the measurement chamber.

In one advantageous configuration of the invention, the measurement chamber is realized in the form of a flow-through measurement chamber with an interior cavity, at least one inlet opening and at least one outlet opening. In the measurement chamber, biomolecules or biocomponents, for example, can then be examined and supplied with a nutrient fluid by means of the inlet and outlet opening. The biomolecule can be, for example, nucleic acids or derivates thereof (DNA, RNA, PNA, LNA, oligonucleotides, plasmids, chromosomes), peptides, proteins (enzyme, protein, oligopeptide, cellular receptor proteins and complexes thereof, peptide hormones, antibodies and fragments thereof), carbohydrates and their peptide hormones, antibodies and fragments thereof), carbohydrates and derivatives thereof, in particular glycolized proteins and glycosides, fats, fatty acids and/or lipids.

In one preferred embodiment of the invention, in the interior cavity, at least one receptor for a ligand, in particular for a biomolecule, a biological cell and/or at least one fragment thereof is immobilized on the surface of at least one radiation receiver, whereby the ligand is marked with the at least one luminescent substance. In this case, the term "receptor" means a molecule that can be bonded to a surface and can enter into a bond with a second molecule, the ligand. Receptors include, for example, but are not limited to: nucleic acids and derivatives thereof (DNA, RNA, PNA, LNA, oligonucleotides, plasmids, chromosome), peptides and proteins (enzymes, proteins, oligopeptides, cellular receptor proteins and complexes thereof, peptide hormones, antibodies and fragments thereof), carbohydrates and byproducts thereof, in particular glycolized proteins and glycosides. The receptor, however, can also include more complex structures such as cells and fragments thereof, for example. The term "ligands" as used here means molecules that can form a more or less specific bond with a receptor. Ligands include, for example, but are not limited to: nucleic acids and derivatives thereof (DNA, RNA, PNA, LNA, oligonucleotides, plasmids, chromosomes), peptides and proteins (enzymes, proteins, oligopeptides, cellular receptor proteins and complexes thereof, peptide hormones, antibodies and fragments thereof, carbohydrates and derivatives thereof, in particular glycolized proteins and glycosides, gats, fatty acids and lipids, cells and fragments thereof, as well as all pharmacologically and toxicologically active substances. The receptor can be imprinted on the radiation receiver, if necessary. A polyimide layer can be placed between the radiation receiver and the receiver to improve the adherence of the receptor to the radiation receiver.

It is advantageous if there are a plurality of radiation receivers on the semiconductor substrate, preferably in the form of a two-dimensional array, arranged next to one another, and if different receptors are located on the radiation receivers, if necessary. The device then makes it possible to examine analytes for the presence of a number of different ligands.

It is particularly advantageous if at least two of the different receptors have a different affinity for at least one ligand marked with the luminescent substance, and if, optionally, there are more than two receptors that have a graduated affinity for the at least one ligand. A radiation receiver on which a receptor with a high affinity for the ligand is located then delivers a measurement signal even at a low concentration of the ligand in an analyte to be tested in the measurement chamber. A radiation receiver on which a receptor with a low affinity to the ligand is located delivers a measurement signal only at a correspondingly higher concentration of the ligand if the measurement signal from the first above named radiation receiver is already at saturation. A device that has a corresponding number of receptors with graduated affinity thus makes possible a determination of the concentration of the ligands over a wide dynamic range. The device thereby makes it possible to perform a measurement of the concentration of the ligand with great accuracy both on ligands that are present in a high concentration and also on ligands that are present in a low concentration, without the requirement for the complex and time-consuming dilution of the ligand. The receptors can be antibodies that are applied against various epitopes of the same ligand on the individual radiation receivers but have different bonding constants. It is also possible, however, for the affinity of at least one antibody to be reduced by a chemical treatment.

The invention is explained in greater detail below, with reference to the exemplary embodiments of the invention illustrated in the accompanying drawings, several of which are only schematic:

DETAILED DESCRIPTION OF THE PREFERRED EMBODIMENTS

Figure 1:
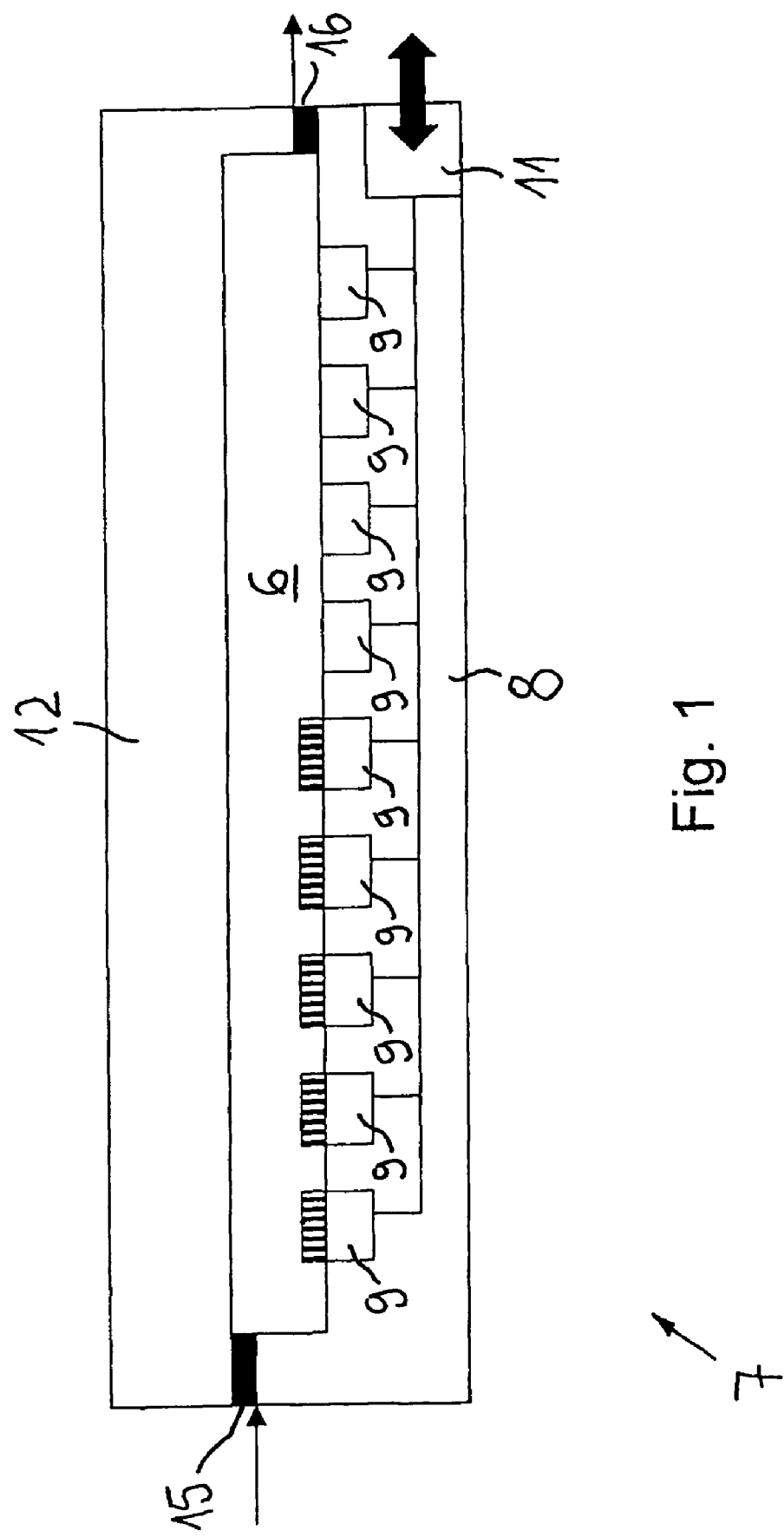
FIG. 1 is a cross section through a flow-through measurement chamber, in the interior cavity of which there is a luminescent substance, whereby the flow-through measurement chamber has radiation receivers for the measurement of the luminescent radiation.

A device designated 1 overall for the detection of at least one luminescent substance 2 has a radiation source 3 which is shown only schematically in the drawing, and which is located and oriented so that an excitation radiation 4 emitted by it strikes the luminescent substance 2. The radiation source 3 can be a semiconductor radiation source, for example, in particular a light-emitting diode or a laser diode. The spectrum of the excitation radiation 4 has at least one excitation wavelength at which the luminescent substance 2 is excited to emit luminescent radiation 5.

The luminescent substance 2 is located in the interior cavity 6 of a measurement chamber 7, the walls of which are essentially impermeable for the luminescent radiation 5. The measurement chamber 7 has a wall area that faces the radiation source 3 and is permeable to the excitation radiation 4 and is formed by a disc-shaped or plate-shaped silicon semiconductor substrate 8. The semiconductor substrate 8 can be economically manufactured from a silicon wafer during the fabrication of the measurement chamber 7.

Figure 2:
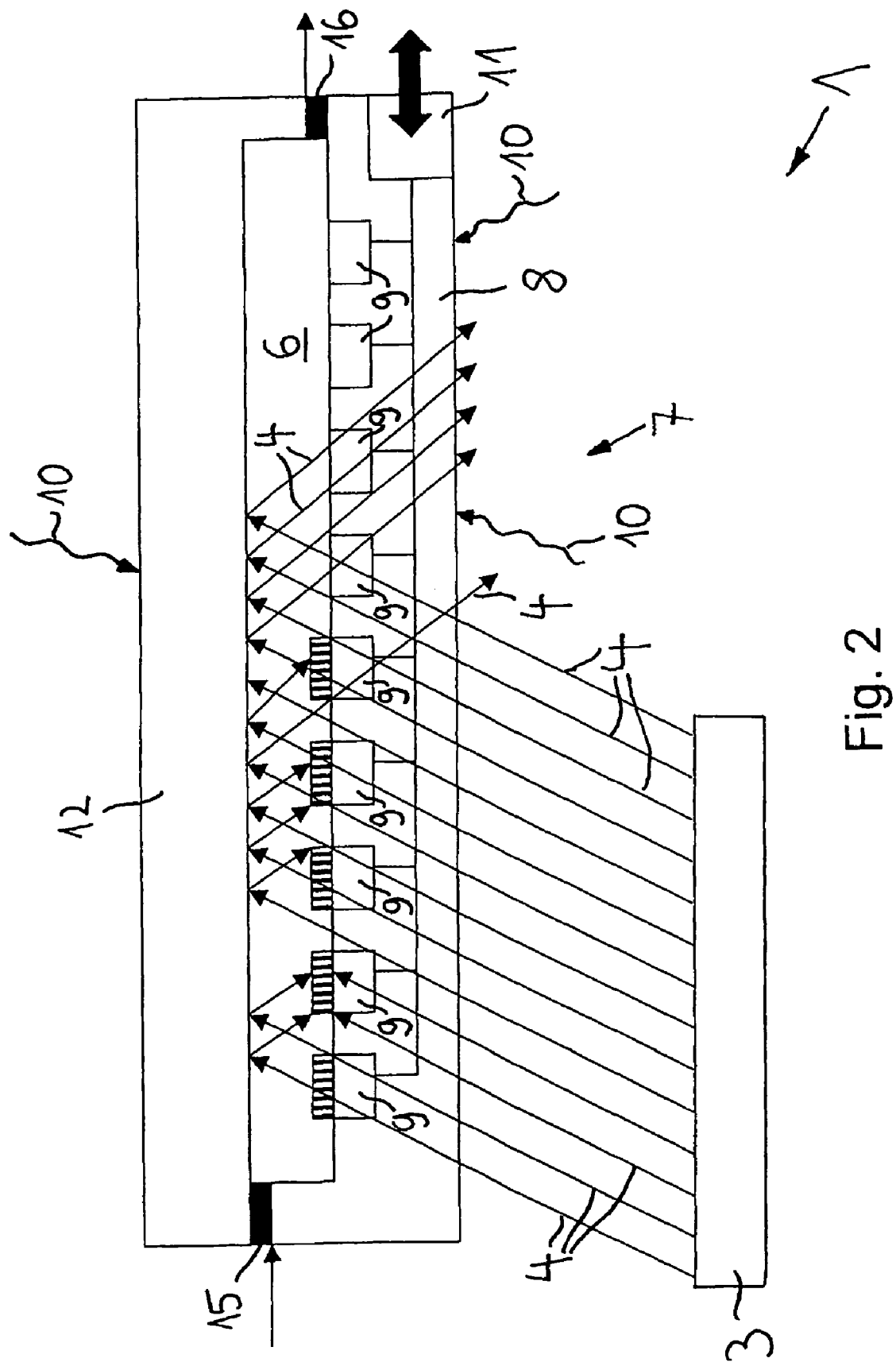
FIG. 2 is a cross section through a device with a flow-through measurement chamber that has a wall area that is permeable for an excitation radiation and faces a reflective boundary wall, whereby the excitation radiation is illustrated schematically in the form of beams.

FIG. 2 shows that the radiation source 3 is located outside the measurement chamber 7, and that the excitation radiation 4 is injected through the semiconductor substrate 8 into the interior cavity 6 of the measurement chamber 7. For the detection of the luminescent radiation 5 emitted by the luminescent substance 2, a plurality of radiation receivers 9 that are realized in the form of photo diodes are located on the semiconductor substrate 8, and with their detection side face the interior cavity 6 of the measurement chamber 7.

Figure 7:
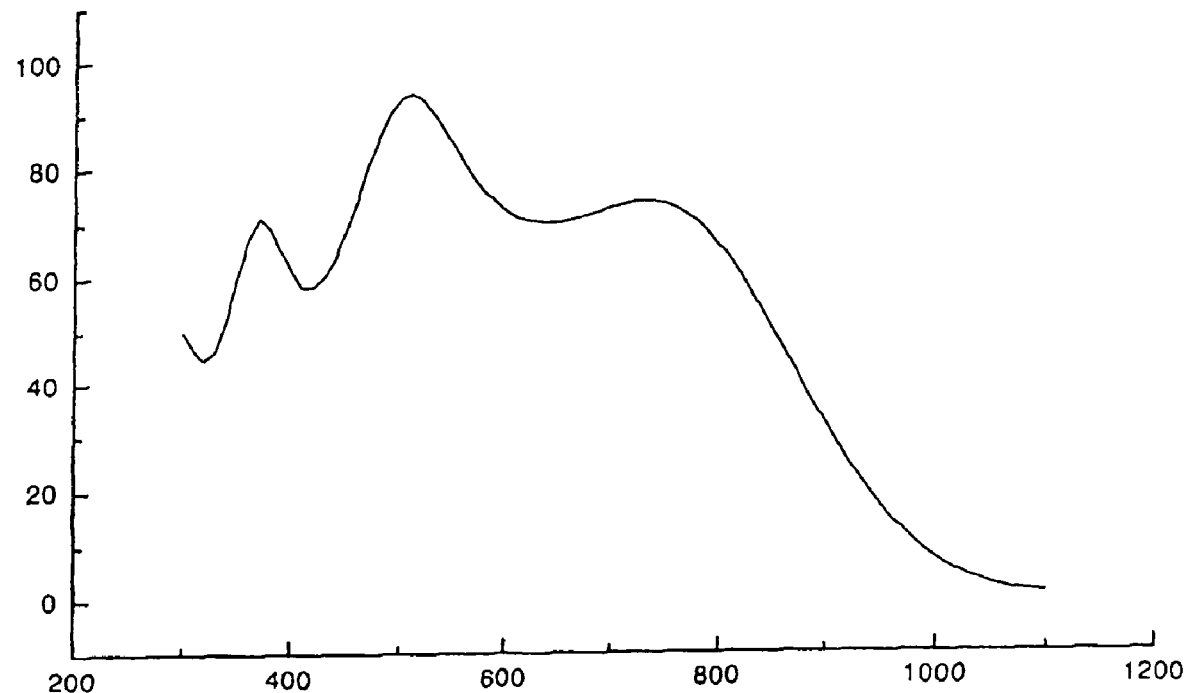
FIG. 7 is a graphical presentation of the spectral sensitivity of a photodiode, whereby the wavelength in nanometers is plotted on the abscissa and the quantum efficiency in percent is plotted on the ordinate.

The spectral distribution of the excitation radiation 4 lies in a wavelength range that is above approximately 1080 nm. As shown in FIG. 7, the radiation receivers 9 are insensitive in this wavelength range. The luminescent substance 2 is an upward-converting luminescent substance 2 in which the wavelength of the luminescent radiation 5 is less than the wavelength of the excitation radiation 3. The energy required for the emission of a luminescent radiation quanta is thereby acquired from a plurality of radiation quanta of the radiation source 3. The spectrum of the luminescent radiation lies in a wavelength range below 1080 nm, in which the radiation receivers 9 are sensitive. The radiation receivers 9 therefore detect only the luminescent radiation 5 and not the excitation radiation 4. The measurement chamber 7 is essentially impermeable for radiation that lies in the wavelength range in which the radiation receivers 9 are sensitive. Thus the radiation receivers 9 are shielded by the measurement chamber 7 against interference radiation 10 that occurs outside the measurement chamber 7.

Figure 3:
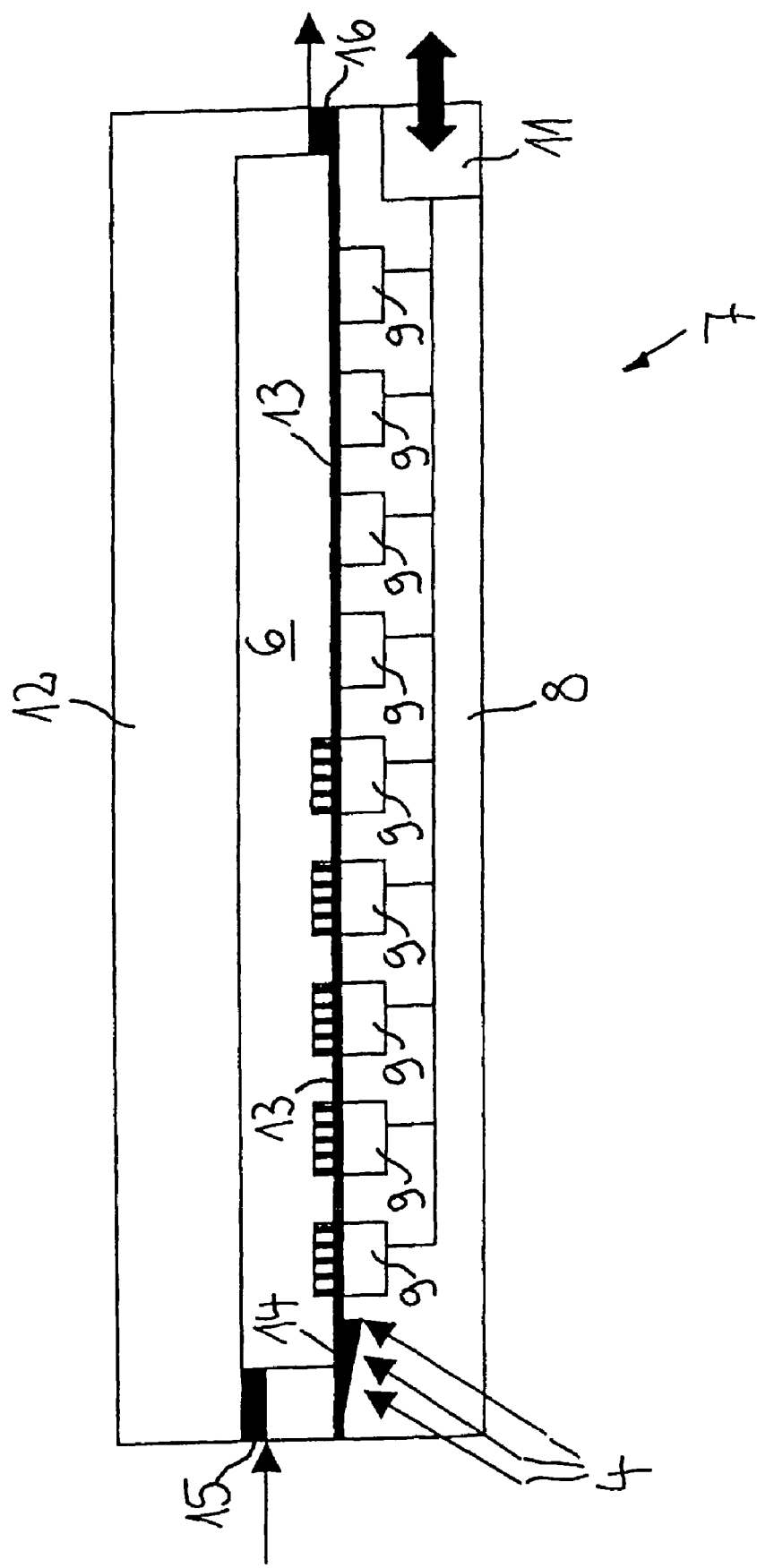
FIG. 3 is a cross section through a flow-through measurement chamber that has a wall area realized in the form of a waveguide, in which the excitation radiation is guided.

FIGS. 1 to 3 show that the radiation receivers 9 are connected by means of printed conductors with an actuator and analysis device 11 that is integrated into the semiconductor substrate. The analysis device 11 has an interface device, which is illustrated schematically in the drawing, for the connection with a higher-level display and/or analysis unit, such as a microcomputer, for example.

In the exemplary embodiment illustrated in FIG. 2, the boundary wall 12 of the measurement chamber 7 that faces the semiconductor substrate 8 is realized in the form of a reflector, on which the excitation radiation 4 injected through the semiconductor substrate into the interior cavity 6 of the measurement chamber 7 is reflected back into the interior cavity 6. The excitation radiation 4 injected into the measurement chamber 7 is thereby conducted through the measurement chamber 7 a plurality of times and can thus be utilized more efficiently for the excitation of the luminescent substance 2. The boundary wall 12 has a base body made of silicon which is provided with a coating that reflects the excitation radiation 4 on its inside facing the interior cavity 6.

In the exemplary embodiment illustrated in FIG. 3, the semiconductor substrate 8 is connected by means of an optical waveguide 13 with the interior cavity of the measurement chamber 7. The excitation radiation 4—starting from the radiation source to the interior cavity 6—first penetrates the semiconductor substrate 8 and then arrives at an optical window of the waveguide 13, at which the excitation radiation 4 is injected into the waveguide 13. The optical window is provided on a prism-shaped injection element 14. The waveguide 13 is realized in the form of a waveguide stratum that runs approximately parallel to the plane of extension of the semiconductor substrate 8 and is located on the inside of the semiconductor 8 that faces the interior cavity 6. In the exemplary embodiment illustrated in FIG. 3, the waveguide stratum 13 extends without interruption over the radiation receivers 9. Other embodiments are also conceivable, however, in which the waveguide stratum 13 can have interruptions or discontinuities in the vicinity of the radiation receivers 9. The luminescent substance is excited by means of the evanescence field of the excitation radiation 4 guided in the waveguide 13, which extends into the interior cavity 6.

FIGS. 1 to 3 also show that the measurement chamber 7 is realized in the form of a flow cell or flow-through measurement chamber with an inlet opening 15 and an outlet opening 16. Detection reactions can be performed in the measurement chamber 7.

Figure 4:
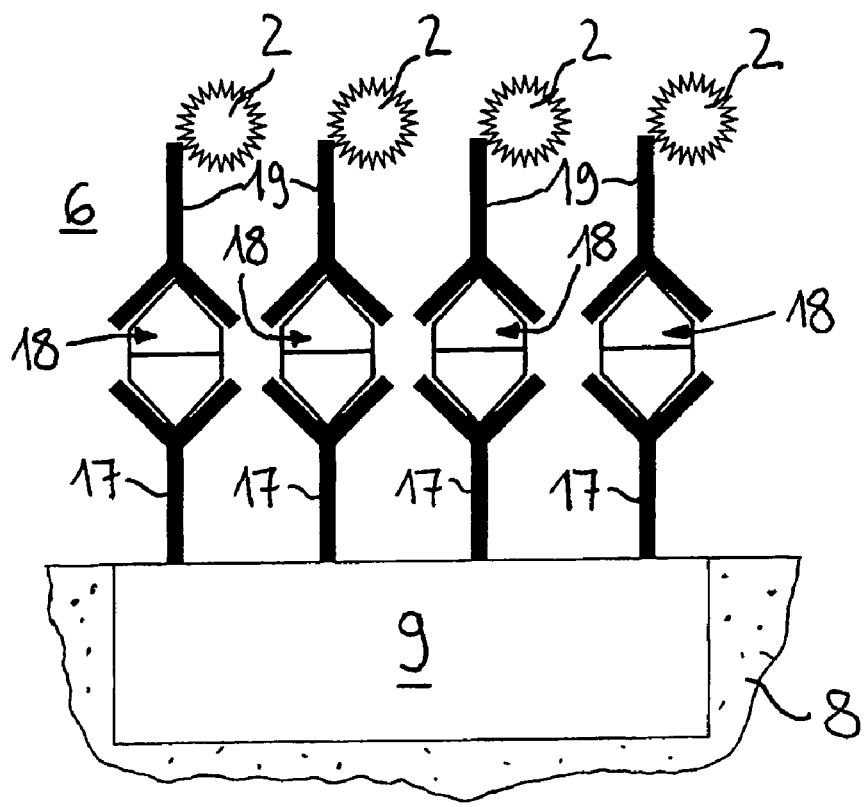
FIG. 4 is a cross section through a radiation receiver on which a receptor layer is immobilized, which binds ligands marked by a luminescent substance.
Figure 5:
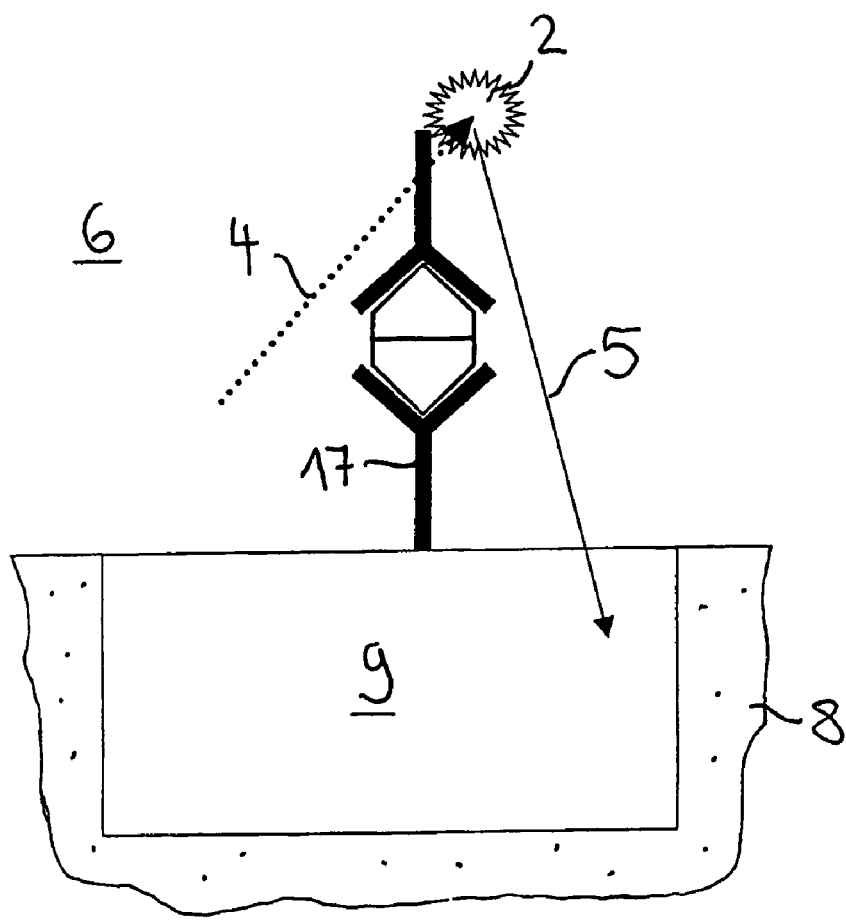
FIG. 5 is an illustration similar to FIG. 4, whereby the luminescent substance is excited by means of excitation radiation for the emission of luminescent radiation, whereby the excitation radiation and the luminescent radiation is illustrated schematically in the form of beams.

FIG. 4 shows that in the interior cavity of the measurement chamber, a receptor 17 is immobilized on the radiation receiver 9, which receptor bonds to a specific ligand. The immobilization of the receptor 17 can be achieved by, for example, a silanization or by a polyimide layer located on the radiation receiver 9, to which layer the receptor 17 adheres. The receptor 17 can be imprinted on the radiation receiver 9 or on the polyimide layer that is located on it. In the exemplary embodiment illustrated in FIG. 4, the receptor 17 is a first antibody against a determined epitope 18 of the ligand. After the bonding of the epitope 18 to the receptor 17, the resulting antibody complex formed by the epitope 18 and the receptor 19 is marked by means of a second antibody 19 that bonds to the epitope 18. This antibody 19 is marked directly or indirectly with the luminescent substance 2. The luminescent substance 2 can be a fluorescing due, for example.

Figure 6:
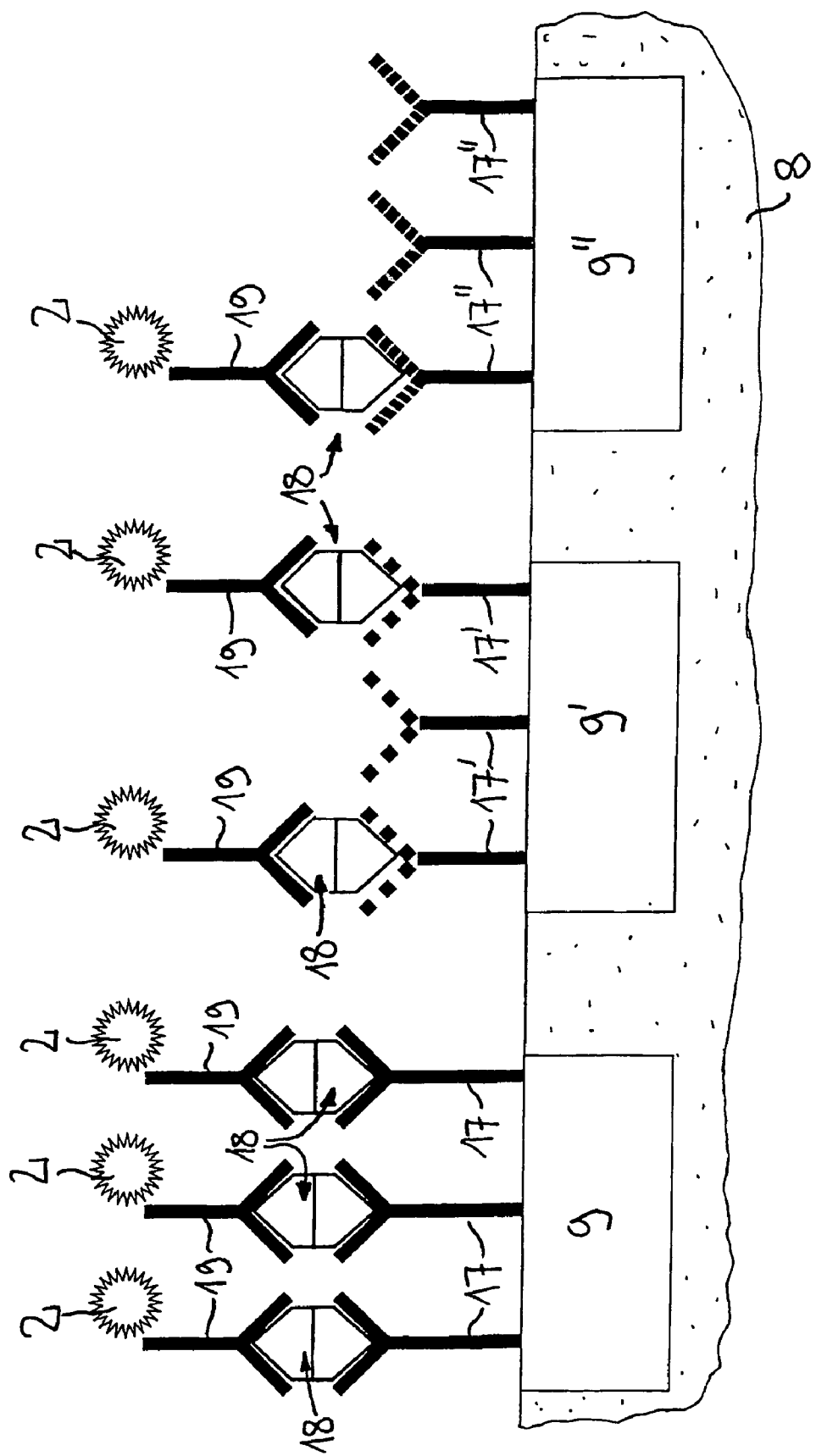
FIG. 6 is a partial cross section through a wall area of the measurement chamber which has a plurality of radiation receivers on which receptors are immobilized.

In the exemplary embodiment illustrated in FIG. 6, the semiconductor substrate 8 has a plurality of radiation receivers 9, 9', 9"[1] located next to one another, on which different receptors 17, 17', 17" are immobilized. The receptors are selected so that they have a different, graduated affinity for a determined ligand. The receptor 17 thereby has a high affinity, the receptor 17' an intermediate affinity and the receptor 17" a low affinity for the epitope 18 of the ligand. Accordingly, a greater number of ligands bond to the receptor 17 than to the receptor 17'. In a corresponding manner, the number of ligands that bond to the receptor 17' is greater than the number of ligands that bond to the receptor 17". Because the ligands are marked with the luminescent substance 2 and this luminescent substance is excited by means of the radiation source 3 to emit luminescent radiation, there is a greater intensity of the luminescent radiation on the radiation receiver 9 than on the radiation receiver 9'. In a corresponding manner, the intensity of the luminescent radiation on the radiation receiver 9' is greater than on the radiation receiver 9". It is therefore possible to determine the concentration of the ligands from the measurement signals from the radiation receivers 9, 9', 9". Because of the graduated affinity of the different receptors 17, 17', 17", the device 1 makes it possible to determine the concentration of the ligands over a wide dynamic range.

[1] Translator's Note: In the German text, the references 9, 9, 9 and 17, 17, 17 are written as series of three identical numbers. From the spacing of the characters it is likely that they should be 9, 9', 9" and 17, 17', 17", although there are no ' or " characters in the description. In the claims, however, they are written 9, 9', 9. The translation assumes they should be 9, 9', 9" and 17, 17', 17" throughout.

The device 1 for the detection of at least one luminescent substance 2 therefore has a radiation source 3 for the emission of excitation radiation 4 on the at least one luminescent substance 2. The excitation radiation 4 has at least one excitation wavelength at which the luminescent substance 2 is excited to the emission of luminescent radiation 5. For the detection of the luminescent radiation 5, there is at least one radiation receiver 9, 9', 9", which is realized with reference to its spectral sensitivity so that it is insensitive to the excitation radiation 4 emitted by the radiation source 3. The luminescent substance 2 is in the interior of a measurement chamber 7 which is essentially impermeable to the luminescent radiation 5, whereby the measurement chamber 7 has at least one transparent wall area that is transparent for the excitation radiation 4 emitted by the radiation source 3. The radiation source 3 is therefore located outside the measurement chamber 7 such that the excitation radiation 4 emitted by the radiation source 3 is injected through the wall area into the interior of the measurement chamber 7.

The invention claimed is:

1. A device for the detection of at least one luminescent substance, with a radiation source for the emission of excitation radiation on the at least one luminescent substance, whereby the excitation radiation has at least one excitation wavelength at which the luminescent substance is excited to emit luminescent radiation, and with at least one radiation receiver which is insensitive to the excitation radiation, for the detection of the luminescent radiation, whereby the luminescent substance is located in the interior of a measurement chamber which is essentially impermeable to the radiation to which the radiation receivers are sensitive, and whereby the radiation source is located outside the measurement chamber such that the excitation radiation is injected through a wall area of the measurement chamber that faces the radiation source and is transparent for the excitation radiation through the measurement chamber into the interior of the measurement chamber, wherein the wall area is formed by a semiconductor substrate and that the at least one radiation receiver is integrated in the form of a semiconductor assembly into the semiconductor substrate.

2. The device as claimed in claim 1, wherein the luminescent substance is realized so that the wavelength of the luminescent radiation is less than the excitation wavelength.

3. The device as claimed in claim 1, wherein the semiconductor substrate is a silicon substrate.

4. The device as claimed in claim 1, wherein it is realized in the form of a thermal imaging camera that has a plurality of radiation receivers located in the measurement chamber in the form of a two-dimensional matrix, with at least one associated optical imaging system for the imaging of the radiation source on the radiation receivers.

5. The device as claimed in claim 1, wherein a boundary wall of the measurement chamber facing the wall area is realized in the form of a reflector for the reflection of the excitation radiation.

6. The device as claimed in claim 1, wherein the transparent wall area is connected by means of an optical waveguide with the interior of the measurement chamber, and that the waveguide runs parallel to the plane of extension of the transparent wall area, and to its inside facing the luminescent substance.

7. The device as claimed in claim 1, wherein a measurement signal output of at least one radiation receiver is connected with a transponder for the transmission of the measurement signal or of a signal derived from it to a receiver part, and that the transponder is integrated into the semiconductor substrate.

8. The device as claimed in claim 1, wherein in the interior of the measurement chamber there are at least two luminescent substances with excitation wavelengths that are different from each other, and that associated with each of these luminescent substances there are radiation sources with a spectral distribution adapted to the excitation wavelength of the respective luminescent substance.

9. The device as claimed in claim 1, wherein the measurement chamber is realized in the form of a flow-through measurement chamber with an interior cavity, at least one inlet opening and at least one outlet opening.

10. The device as claimed in claim 1, wherein in the interior cavity, on the surface of at least one radiation receiver, at least one receptor for a ligand, a biomolecule, a biological cell and/or at least one fragment of such a ligand, biomolecule or cell is immobilized, and wherein the ligand is marked with the at least one luminescent substance.

11. The device as claimed in claim 3, wherein a plurality of radiation receivers are located next to one another, in the form of a two-dimensional array, on the semiconductor substrate, and that different receptors are optionally located on the radiation receivers.

12. The device as claimed in claim 10, wherein at least two of the different receptors have a different affinity for at least one ligand marked with the luminescent substance, and that optionally more than two receptors are provided that have a graduated affinity for the at least one ligand.

* * * * *